(12) United States Patent
Reeder et al.

(10) Patent No.: US 10,743,791 B2
(45) Date of Patent: Aug. 18, 2020

(54) SYSTEM AND METHOD FOR ASSESSING TISSUE PROPERTIES USING MAGNETIC RESONANCE IMAGING

(71) Applicant: Wisconsin Alumni Research Foundation, Madison, WI (US)

(72) Inventors: Scott B. Reeder, Madison, WI (US); Roberta M. Strigel, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1268 days.

(21) Appl. No.: 14/981,710

(22) Filed: Dec. 28, 2015

(65) Prior Publication Data
US 2017/0181656 A1 Jun. 29, 2017

(51) Int. Cl.
| | | |
|---|---|---|
| *G01R 33/00* | (2006.01) | |
| *A61B 5/055* | (2006.01) | |
| *A61B 5/00* | (2006.01) | |
| *G01R 33/48* | (2006.01) | |
| *G06T 7/00* | (2017.01) | |
| *G01R 33/485* | (2006.01) | |
| *G01R 33/56* | (2006.01) | |

(52) U.S. Cl.
CPC .......... *A61B 5/055* (2013.01); *A61B 5/4312* (2013.01); *A61B 5/4872* (2013.01); *A61B 5/4875* (2013.01); *A61B 5/7282* (2013.01); *G01R 33/485* (2013.01); *G01R 33/4828* (2013.01); *G06T 7/0012* (2013.01); *A61B 2576/02* (2013.01); *G01R 33/5608* (2013.01); *G06T 2207/10088* (2013.01); *G06T 2207/30068* (2013.01)

(58) Field of Classification Search
CPC .... A61B 5/055; A61B 5/7282; G01R 33/4828
See application file for complete search history.

(56) References Cited

U.S. PATENT DOCUMENTS

| | | | |
|---|---|---|---|
| 2005/0215882 A1* | 9/2005 | Chenevert | A61B 5/055 600/410 |
| 2012/0268120 A1 | 10/2012 | Hernando | |
| 2014/0142417 A1 | 5/2014 | Reeder et al. | |

OTHER PUBLICATIONS

Hernando, et al., Addressing Phase Errors in Fat-Water Imaging Using a Mixed Magnitude/Complex Fitting Method, Magnetic Resonance in Medicine, 2012, 67:638-644.
Ledger, et al., Comparison of Dixon Sequences for Estimation of Percent Breast Fibroglandular Tissue, PLoS ONE, 2016, 11(3):e0152152, 14 pages.
Liu, et al., Fat Quantification With IDEAL Gradient Echo Imaging: Correction of Bias from T1 and Noise, Magnetic Resonance in Medicine, 2007, 58:354-364.

(Continued)

*Primary Examiner* — Joseph M Santos Rodriguez
(74) *Attorney, Agent, or Firm* — Quarles & Brady LLP

(57) ABSTRACT

A system and method for assessing tissue properties of a subject within a region of interest (ROI) using a magnetic resonance imaging (MRI) system includes acquiring chemical-shift-encoded imaging data of the ROI. The method also includes determining, from imaging data a proton density water fraction (PDWF) map and quantifying, using the PDWF map, a property of tissue within the ROI. The method further includes generating, using the PDWF map, a report indicating the quantified property of the tissue. The tissue may include fibroglandular tissue (FGT).

28 Claims, 4 Drawing Sheets

(56) References Cited

OTHER PUBLICATIONS

Reeder, et al., Proton Density Fat-Fraction: A Standardized MR-Based Biomarker of Tissue Fat Concentration, Journal of Magnetic Resonance Imaging, 2012, 36:1011-1014.

Strigel, et al., Proton Density Water Fraction as a Measurement of Breast Fibroglandular Tissue Volume and Concentration, Proceedings of the International Society for Magnetic Resonance in Medicine, 24th Annual Meeting and Exhibition, Singapore, May 7-13, 2016, vol. 24, Apr. 23, 2016, p. 2480.

Yu, et al., Multiecho Reconstruction for Simultaneous Water-Fat Decomposition and T2* Estimation, Journal of Magnetic Resonance Imaging, 2007, 26:1153-1161.

Yu, et al., Combination of Complex-Based and Magnitude-Based Multiecho Water-Fat Separation for Accurate Quantification of Fat-Fraction, Magnetic Resonance in Medicine, 2011, 66:199-206.

PCT International Search Report and Written Opinion, PCT/US2016/068649, May 9, 2017.

Chang, et al., Comparison of Breast Density Measured on MR Images Acquired Using Fat-Suppressed Versus Nonfat-Suppressed Sequences, Med. Phys., 2011, 38(11):5961-5968.

Chen, et al., Impact of Positional Difference on the Measurement of Breast Density Using MRI, Med. Phys., 2015, 42(5):2268-2275.

Clendenen; et al., Comparison of 3-Point Dixon Imaging and Fuzzy C-means Clustering Methods for Breast Density Measurement, Journal of Magnetic Resonance Imaging, 2013, 38:474-481.

Graham, et al., Changes in Fibroglandular Volume and Water Content of Breast Tissue Curing the Menstrual Cycle Observed by MR Imaging at 1.5 T, Journal of Magnetic Resonance Imaging, 1995, 5:695-701.

Khazen, et al., A Pilot Study of Compositional Analysis of the Breast and Estimation of Breast Mammographic Density Using Three-Dimensional T1-Weighted Magnetic Resonance Imaging, Cancer Epicierniol, Biomarkers Prev., 2008, 17(9):2268-2274.

Ledger, et al., High-Resolution Proton Density Weighted Dixon Sequences Maximize Precision of Breast Density Measurements, Proc. Intl. Soc. Mag. Reson. Med., 2015, 23:1081.

Lu, et al., Comparison of Breast Tissue Measurements Using Magnetic Resonance Imaging, Digital Mammography and a Mathematical Algorithm, Phys. Med. Biol., 2012, 57(21):6903-6927.

Nie, et al., Development of a Quantitative Method for Analysis of Breast Density Based on Three-Dimensional Breast MRI, Med. Phys., 2008, 35(12):5253-5262.

Nie, et al., Impact of Skin Removal on Quantitative Measurement of Breast Density Using MRI, Med. Phys, 2010, 37(1):227-233.

Wei, et al., Correlation Between Mammographic Density and Volumetric Fibroglandular Tissue Estimated on Breast MR Images, Med. Phys., 2004, 31:933-942.

Wu, et al., Automated Fibroglandular Tissue Segmentation and Volumetric Density Estimation in Breast MRI Using an Atlas-Aided Fuzzy C-means Method, Med. Phys., 2013, 40(12):122302-1 thru 122302-12.

* cited by examiner

SYSTEM AND METHOD FOR ASSESSING TISSUE PROPERTIES USING MAGNETIC RESONANCE IMAGING

STATEMENT REGARDING FEDERALLY SPONSORED RESEARCH

This invention was made with government support under DK083380, DK088925, DK100651 and DK102595 awarded by the National Institutes of Health. The government has certain rights in the invention.

BACKGROUND

The present disclosure relates, generally, to systems and methods for magnetic resonance imaging (MRI) and, more particularly, to systems and methods for assessing tissue density, such as breast tissue density, using MRI.

Early detection of breast cancer with mammography has been shown in multiple randomized controlled trials to decrease mortality from breast cancer. Unfortunately, mammography has limitations and cannot detect all cancers, with approximately 20% of breast cancers occult on mammography. High mammographic breast density has been shown to increase both breast cancer risk and the difficulty in interpreting mammograms. The American College of Radiology (ACR) Breast Imaging and Reporting Data System (BI-RADS) Atlas describes four categories for breast density that are, by nature, subjective: (a) almost entirely fatty; (b) scattered areas of fibroglandular tissue (FGT) density; (c) heterogeneously dense, which may obscure small masses; and (d) extremely dense, which lowers the sensitivity of mammography to detect cancer. Distribution of women by density category is approximately: 10% fatty; 40% scattered fibroglandular; 40% heterogeneously dense; and 10% extremely dense, with 50% of women falling into the two highest categories of breast density as reported by interpreting radiologists in the United States Breast Cancer Surveillance Consortium. The reduction in mammographic sensitivity is approximately 7% for women with heterogeneously dense breasts and 13% for women with extremely dense breasts when compared with women of average breast density. It is well known that the lifetime risk in those patients with mammographically dense breasts is increased compared to those with less dense breasts. While the exact mechanism is not well understood, there is a clear need to risk-stratify patients based on breast density. Unfortunately, using mammography, there is both intra- and inter-observation variation in visually estimated breast density between two adjacent density categories. This is particularly pronounced between the two intermediate categories (b and c), which define whether or not a patient has "dense" breasts. Further, the difference in sensitivity between the least dense breast in a higher density category and the most dense breast in a lower-density category may be insignificant, limiting the clinical usefulness of breast density categorization and highlighting the need for a robust, quantitative measurement of breast density, as a predictor of future development of breast cancer.

Patients with mammographically dense breasts have an increased risk of breast cancer, with women with the highest breast density having an estimated 4- to 6-fold increased risk of breast cancer compared to women with the least dense breasts. The Food and Drug Administration (FDA)'s Mammography Quality and Standards Act (MQSA) requires facilities performing mammography to report a patient's breast density to the referring clinician in the final written report. Patient advocacy groups, such as "Are You Dense?" in the United States, have been influential in getting breast density notification laws enacted, currently active in 24 states. Most state density laws require that patients be informed if they have dense breast tissue and that dense breasts are associated with increased cancer risk. All require a statement indicating that mammography may be more limited in dense breasts.

Mammography quantifies breast density by differentiating between radiographically opaque fibroglandular tissue (stromal and epithelial tissues) and radiographically lucent fat. Several commercially available software packages provide a quantitative measurement of percentage of fibroglandular breast tissue (percentage mammographic density) calculated from the total breast area within a mammogram. These include Cumulus (University of Toronto), Quantra (Hologic Inc., Bedford, Mass.), and Volpara (Matakina). However, there are multiple limitations of mammographic-based methods of measuring breast density, including the impact of compression and breast orientation, using two-dimensional projected area (rather than volume) of tissue, variations in mammographic acquisition parameters, and the use of ionizing radiation. These limitations have limited the clinical use of mammographic breast density quantification software, and have led to interest in measuring breast tissue composition with other modalities.

Magnetic Resonance Imaging (MRI) is a widely available and accessible technology that does not use ionizing radiation. When a substance, such as human tissue, is subjected to a sufficiently large, uniform magnetic field (polarizing field $B_0$), the individual magnetic moments of the nuclei in the tissue attempt to align with this polarizing field, but precess about it in random order at their characteristic Larmor frequency. If the substance, or tissue, is subjected to a magnetic field (excitation field $B_1$) that is in the x-y plane and that is near the Larmor frequency, the net aligned moment, $M_z$, may be rotated, or "tipped", into the x-y plane to produce a net transverse magnetic moment $M_{xy}$. A signal is emitted by the excited nuclei or "spins", after the excitation signal $B_1$ is terminated, and this signal may be received and processed to form an image.

When utilizing these "MR" signals to produce images, magnetic field gradients ($G_x$, $G_y$, $G_z$) are employed. Typically, the region to be imaged is scanned by a sequence of measurement cycles in which these gradients vary according to the particular localization method being used. The resulting set of received MR signals are digitized and processed to reconstruct the image using one of many well known reconstruction techniques.

To do so, the signals are often weighted in different ways to give preference to or consider different sub-signals or so-called contrast mechanisms. Two basic "contrast mechanisms" commonly utilized in MR imaging are the spin-lattice (or longitudinal or $T_1$) relaxation time or spin-spin (or transverse or $T_2$) relaxation time. However, there are a variety of other mechanisms for eliciting contrast in MRI, including $R_2^*$. Specifically, $T_2^*$ is a quantity related to $T_2$, but including dephasing effects. That is, $T_2^*$ is a quantity related to spin-spin relaxation and, in addition, relating magnetic field inhomogeneities and susceptibility effects. Often, instead of $T_2^*$, these quantities are preferably expressed in terms of relaxation, or the inverse of the $T_2^*$ time constant, represented as $R_2^*$. Thus, MRI provides a variety of mechanism that can be used to analyze tissue and is gaining popularity for breast imaging.

MRI has gained popularity for breast imaging for a variety of reasons. For example, breast MRI is the most sensitive modality for the detection of breast cancer, detecting more cancers than mammography, ultrasound, or the physical breast exam. Furthermore, MRI's ability to provide 3D volumetric images that encompass the entire breast means that clinicians can better image breast tissue near the chest wall, without compression. Further still, the different contrast available from MRI allows images to be created that are weighted toward particular tissue types of interest.

Potential benefits of MRI quantification of fibroglandular tissue are multifold. MRI-derived quantification of fibroglandular breast tissue relies on the different relaxation properties of fibroglandular tissue and fat, in contrast to percentage mammographic density derived from X-ray beam attenuation in fibroglandular tissue. Thus, it is likely to have less measurement error than the subjective measurement of breast density from two-dimensional mammography in compression. MRI can be used to measure breast tissue composition in cross-section and MRI can provide three-dimensional, volumetric images without breast compression.

Regardless of imaging modality, valid quantitative imaging biomarkers must satisfy several important metrics of performance including accuracy, precision, robustness, and reproducibility. Any new biomarker must have good technical accuracy for quantifying a relevant tissue property of tissue (e.g. density of fibroglandular tissue). It must also have low variability to repeated measurements, i.e. repeatability, and it must be robust to differences in acquisition parameters such as TR, TE, flip angle, and the like. Further, the method should be reproducible across sites, vendors, and magnetic field strength. A new biomarker that satisfies these requirements and quantifies a fundamental tissue property of clinical relevance can be a valuable biomarker.

Multiple MR-based methods have been described to calculate percentage of fibroglandular tissue. These methods are typically reliant on T1-weighted pulse sequences and include threshold-based segmentation of signal intensities and clustering algorithms such as the fuzzy C-means algorithm. Chemical-shift-encoded MRI (CSE-MRI) "Dixon" fat-water separation techniques have been described, which collect data with at least two different TEs allowing separation of water and fat and result in water-only and fat-only images. More recently, some have compared a fuzzy C-means and a 3-point Dixon segmentation method for calculation of percentage fibroglandular tissue, finding that Dixon measurements were on average 10-20% higher. Thus, variability in percentage of fibroglandular tissue has been reported between methods, segmentation techniques (including inclusion or exclusion of the skin), positioning, and pulse sequences differences (including the use of chemical fat-suppression). Thus, the currently proposed methods do not satisfy the requirements for a valid biomarker as described above.

Therefore, it would be desirable to have a system and method for breast imaging that is capable of providing accurate breast density information and valid quantitative imaging biomarkers.

SUMMARY

The present invention overcomes the aforementioned drawbacks by providing systems and methods for using confounder corrected CSE-MRI techniques to analyze tissue properties, such as to quantify the amount or concentration of fibroglandular tissue in the breast, which can be used as a biomarker of breast density and ultimately risk for the development of breast cancer. Proton density water fraction (PDWF) can used to quantify tissue properties and, more particularly, to quantify fibroglandular tissue amount or concentration in the breast.

In accordance with one aspect of the present disclosure, a method is provided for assessing magnetic tissue properties of a subject within a region of interest (ROI) using a magnetic resonance imaging (MRI) system. The method includes acquiring chemical-shift-encoded imaging data of the ROI and, from the imaging data, determining a proton density water fraction (PDWF) map. The method also includes quantifying a property of tissue within the ROI using the PDWF map and generating a report indicating the quantified property of the tissue using the PDWF map.

In accordance with another aspect of the present disclosure, a magnetic resonance imaging (MRI) system is disclosed that includes a magnet system configured to generate a polarizing magnetic field about at least a portion of a subject arranged in the MRI system, a plurality of gradient coils configured to apply a gradient field to the polarizing magnetic field, and a radio frequency (RF) system configured to apply an excitation field to the subject and acquire MR image data from a ROI. The system also includes a computer system programmed to receive chemical-shift-encoded data of the ROI acquired using the RF system and gradient coils, analyze the chemical-shift-encoded data to determine water component and a fat component and, using the chemical-shift-encoded data, the water component, and the fat component, determine a proton density water fraction (PDWF) map. The computer is also programmed to quantify a property of tissue within the ROI using the PDWF map and generate a report indicating the quantified property of the tissue using the PDWF map.

The foregoing and other aspects and advantages of the invention will appear from the following description. In the description, reference is made to the accompanying drawings, which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

Figure 1:
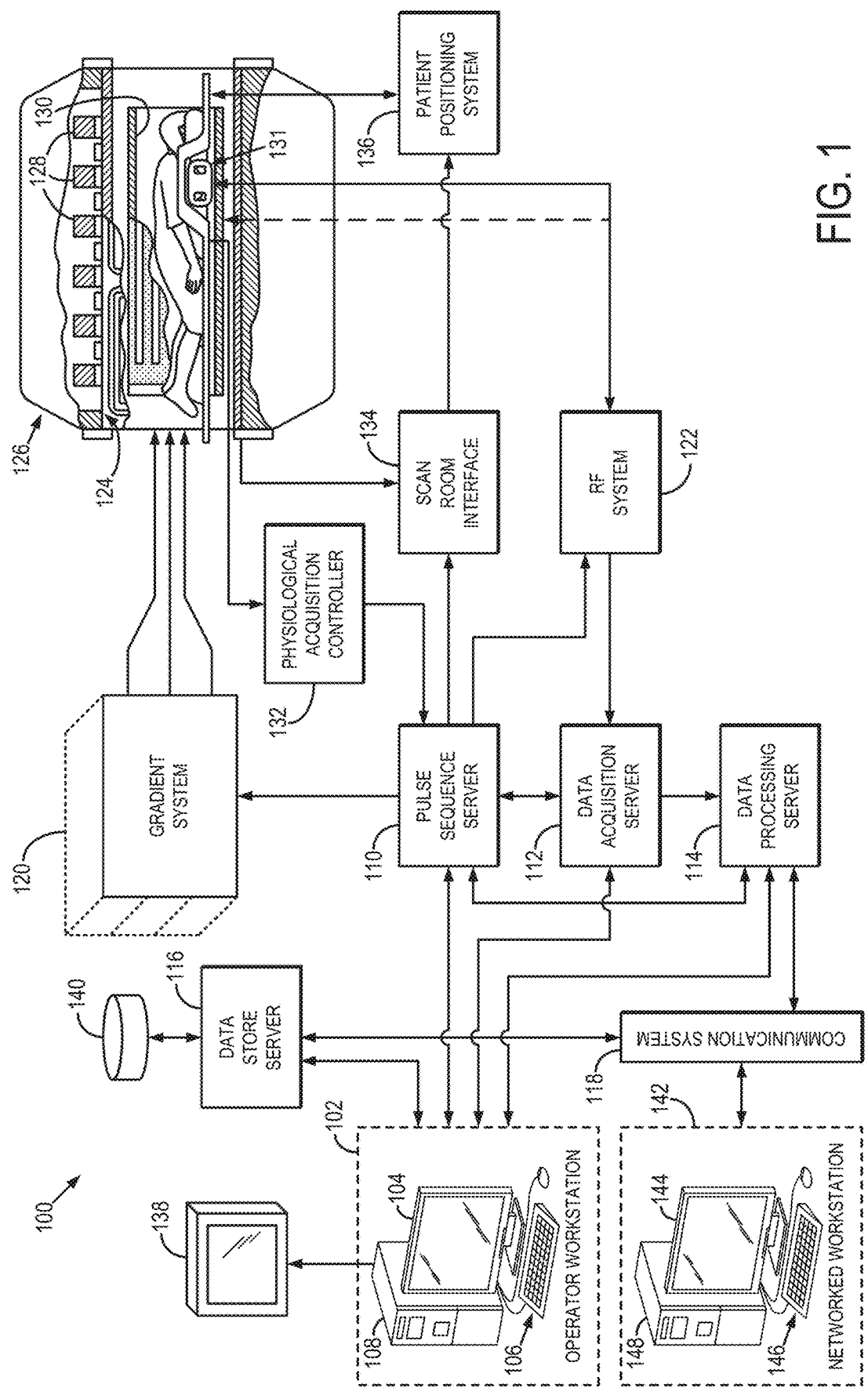
FIG. 1 is a block diagram of an exemplary magnetic resonance imaging (MRI) system that employs the present disclosure.

Referring to FIG. 1, an example of a magnetic resonance imaging ("MRI") system 100 is illustrated. The MRI system 100 includes an operator workstation 102, which will typically include a display 104, one or more input devices 106 (such as a keyboard and mouse), and a processor 108. The processor 108 may include a commercially available programmable machine running a commercially available operating system. The operator workstation 102 provides the operator interface that enables scan prescriptions to be entered into the MRI system 100. In general, the operator workstation 102 may be coupled to multiple servers including a pulse sequence server 110, a data acquisition server 112, a data processing server 114, and a data store server 116. The operator workstation 102 and each server 110, 112, 114, and 116 are connected to communicate with each other. For example, the servers 110, 112, 114, and 116 may be connected via a communication system 118, which may include any suitable network connection, whether wired, wireless, or a combination of both. As an example, the communication system 118 may include both proprietary or dedicated networks, as well as open networks, such as the internet.

The pulse sequence server 110 functions in response to instructions downloaded from the operator workstation 102 to operate a gradient system 120 and a radiofrequency (RF) system 122. Gradient waveforms necessary to perform the prescribed scan are produced and applied to the gradient system 120, which excites gradient coils in an assembly 124 to produce the magnetic field gradients $G_x$, $G_y$, $G_z$, used for position encoding magnetic resonance signals. The gradient coil assembly 124 forms part of a magnet assembly 126 that includes a polarizing magnet 128 and a whole-body RF coil 130 or local RF coil 131.

In operation, RF waveforms are applied by the RF system 122 to the RF coil 130 or 131, in order to perform the prescribed magnetic resonance pulse sequence. Responsive magnetic resonance signals detected by the RF coil 130 or 131 are received by the RF system 122, where they are amplified, demodulated, filtered, and digitized under direction of commands produced by the pulse sequence server 110. As will be described in further detail, the generated RF pulses may be applied using the local breast coil 131 or, in some cases, may also employ the whole-body RF coil 130.

The RF system 122 may also include one or more RF receiver channels. Each RF receiver channel includes an RF preamplifier that amplifies the magnetic resonance signal received by the coil 130 or 131 to which it is connected, and a detector that detects and digitizes the I and Q quadrature components of the received magnetic resonance signal. The magnitude of the received magnetic resonance signal may, therefore, be determined at any sampled point by the square root of the sum of the squares of the I and Q components:

$$M=\sqrt{I^2+Q^2} \tag{1}$$

and the phase of the received magnetic resonance signal may also be determined according to the following relationship:

$$\varphi = \tan^{-1}\left(\frac{Q}{I}\right). \tag{2}$$

The pulse sequence server 110 also optionally receives patient data from a physiological acquisition controller 132. By way of example, the physiological acquisition controller 132 may receive signals from a number of different sensors connected to the patient, such as electrocardiograph ("ECG") signals from electrodes, or respiratory signals from a respiratory bellows or other respiratory monitoring device. Such signals are typically used by the pulse sequence server 110 to synchronize, or "gate," the performance of the scan with the subject's heart beat or respiration.

The pulse sequence server 110 also connects to a scan room interface circuit 134 that receives signals from various sensors associated with the condition of the patient and the magnet system. It is also through the scan room interface circuit 134 that a patient positioning system 136 receives commands to move the patient to desired positions during the scan.

The digitized magnetic resonance signal samples produced by the RF system 122 are received by the data acquisition server 112. The data acquisition server 112 operates in response to instructions downloaded from the operator workstation 102 to receive the real-time magnetic resonance data and provide buffer storage, such that no data is lost by data overrun. In some scans, the data acquisition server 112 does little more than pass the acquired magnetic resonance data to the data processor server 114. However, in scans that require information derived from acquired magnetic resonance data to control the further performance of the scan, the data acquisition server 112 is programmed to produce such information and convey it to the pulse sequence server 110. For example, during prescans, magnetic resonance data is acquired and used to calibrate the pulse sequence performed by the pulse sequence server 110.

The data processing server 114 receives magnetic resonance data from the data acquisition server 112 and processes it in accordance with instructions downloaded from the operator workstation 102. Such processing may, for example, include one or more of the following: reconstructing two-dimensional or three-dimensional images by performing a Fourier transformation of raw k-space data; performing other image reconstruction algorithms, such as iterative or backprojection reconstruction algorithms; applying filters to raw k-space data or to reconstructed images; generating functional magnetic resonance images; calculating motion or flow images; and so on.

Images reconstructed by the data processing server 114 are conveyed back to the operator workstation 102 where they are available for review. Real-time images can be output to operator display 104 or a display 138 that is located near the magnet assembly 126 for use by attending physicians. Batch mode images or selected real time images are stored in a host database on disc storage 140. When such images have been reconstructed and transferred to storage, the data processing server 114 notifies the data store server 116 on the operator workstation 102. The operator workstation 102 may be used by an operator to archive the images, produce films, or send the images via a network to other facilities.

The MRI system 100 may also include one or more networked workstations 142. By way of example, a networked workstation 142 may include a display 144, one or more input devices 146 (such as a keyboard and mouse), and a processor or controller 148. The networked workstation 142 may be located within the same facility as the operator workstation 102, or in a different facility, such as a different healthcare institution or clinic.

The networked workstation 142, whether within the same facility or in a different facility as the operator workstation 102, may gain remote access to the data processing server 114 or data store server 116 via the communication system 118. Accordingly, multiple networked workstations 142 may have access to the data processing server 114 and the data store server 116. In this manner, magnetic resonance data, reconstructed images, or other data may be exchanged between the data processing server 114 or the data store server 116 and the networked workstations 142, such that the data or images may be remotely processed by a networked workstation 142. This data may be exchanged in any suitable format, such as in accordance with the transmission control protocol ("TCP"), the internet protocol ("IP"), or other known or suitable protocols.

In recent years, confounder-corrected chemical shift encoded MRI (CC CSE-MRI) methods have been developed for quantifying the concentration of fat in tissues such as liver, pancreas, and muscle. These techniques can be used to address or correct for potential confounders that negatively impact the accuracy, precision, robustness, and reproducibility of MR-based biomarkers of tissue fat concentration. As will be explained, these methods account or correct for the confounding effects of T1 recovery, T2* decay, spectral complexity of fat, noise bias, and eddy currents, and can be used to address concomitant gradients. When these factors are accounted for or corrected, accurate estimation of the proton density fat fraction (PDFF) is possible. PDFF is a fundamental property of tissue fat concentration. PDFF has been demonstrated to be highly reproducible across platforms, field strength, adults and children, and has been validated extensively in phantoms, animals, explanted human liver tissue, and in multiple studies in human subjects.

As will be described, the present disclosure provides systems and methods to use confounder corrected CSE-MRI techniques to quantify the amount and/or concentration of fibroglandular tissue in the breast, as a biomarker of breast density and ultimately risk for the development of breast cancer. Rather than measuring PDFF, the proton density water fraction (PDWF) can be measured using confounder corrected CSE-MRI techniques. Thus, a system and method is provided to use CSE-MRI-based estimation of PDWF to quantify tissue properties and, more particularly, to quantify fibroglandular tissue amount and/or concentration in the breast.

The present disclosure recognizes that the quantity of physiologically relevant fibroglandular tissue contains water but no adipose tissue. Thus, the majority of water-based MR signal from the breast originates from fibroglandular tissue. If the estimation of water-based tissue is independent of relaxation parameters, the proton water density should reflect the volume and density of physiologically relevant fibroglandular tissue in the breast. Using confounder correct CSE-MRI techniques, separated fat and water images that reflect the proton densities of fat and water, respectively, can be achieved. In this way, by correcting for known confounders of tissue, the estimation of separated water and fat images can be robust to differences in acquisition parameters and reproducible across platforms, vendors, sites and field strength.

As defined herein, PDWF is given by:

$$\eta_W(r) = \frac{W(r)}{F(r) + W(r)}; \quad (3)$$

where $W(r)$ and $F(r)$ are the proton density maps of unconfounded mobile water and mobile triglycerides, respectively. The PDWF map is analogous to the PDWF, but provides a quantitative map of water-based tissue.

In particular, by definition, a material with volume susceptibility $\chi^V$ (unit-less, superscript "V" denotes volume susceptibility), can induce additional magnetic field, $B_{o,in}$, when placed in an external magnetic field $B_0$. That is, the relationship is:

$$B_{o,in} = \chi^V B_o \quad (4).$$

Further, since the susceptibility of a material depends on the concentration of the material, the induced magnetic field can be written as:

$$B_{o,in} = \chi^M [T] B_o \quad (5);$$

where $\chi^M$ is the molar susceptibility (superscript "M" denotes molar, units=m$^3$/mol or ml/mol) of substance T, and [T] is the concentration of substance T (units=mol/m$^3$ or mol/ml). Note that molar susceptibility is related to volume susceptibility using the molecular weight (MW, units=g/mol or kg/mol) and density (units=g/ml or kg/m$^3$) as:

$$\chi^M = \chi^V MW/\rho \quad (6).$$

Alternatively, the mass susceptibility, $\chi^g$ (units=m$^3$/kg or ml/g) can be used, and is related to volume susceptibility as:

$$\chi^g = \chi^V/\rho \quad (7).$$

The change in magnetic field will be a linear combination of the contribution from all substances in the tissue. For example, in liver containing various concentrations (denoted by [–]) of iron (Fe), water (W), fat (F), and non-iron MR invisible material (I) the observed susceptibility would be the weighted sum of the component susceptibilities, such as:

$$\chi_{obs}^V = \chi_W^M[W] + \chi_F^M[F] + \chi_I^M[I] + \chi_{Fe}^M[Fe] \quad (8).$$

Note that, although only water and fat actually produce MR signal, all substances present in the tissue can impact the magnetic susceptibility.

Using chemical shift encoded imaging, the PDFF and PDWF fractions can be measured as:

$$\eta_F^{PDFF} = \frac{[F]}{[F]+[W]}, \eta_W^{PDWF} = \frac{[W]}{[F]+[W]}. \quad (9)$$

If the fraction of MR invisible material is known, then it is possible to determine the volume fraction of water, fat, and MR invisible material, as:

$$\eta_F^V = \frac{[F]}{[F]+[W]+[I]}, \eta_W^V = \frac{[W]}{[F]+[W]+[I]}, \quad (10)$$

$$\eta_I^V = \frac{[I]}{[F]+[W]+[I]}.$$

The above is but one non-limiting example. The water and fat proton density maps can be estimated using any of a variety of advanced confounder-corrected CSE-MRI methods, and can be combined using a magnitude discrimination based technique to avoid noise related bias at low or at high water proton densities. As one examiner of a non-limiting alternative, instead of directly determining PDWF, PDFF can be calculated and PDWF calculated as 1–PDFF.

Figure 2:
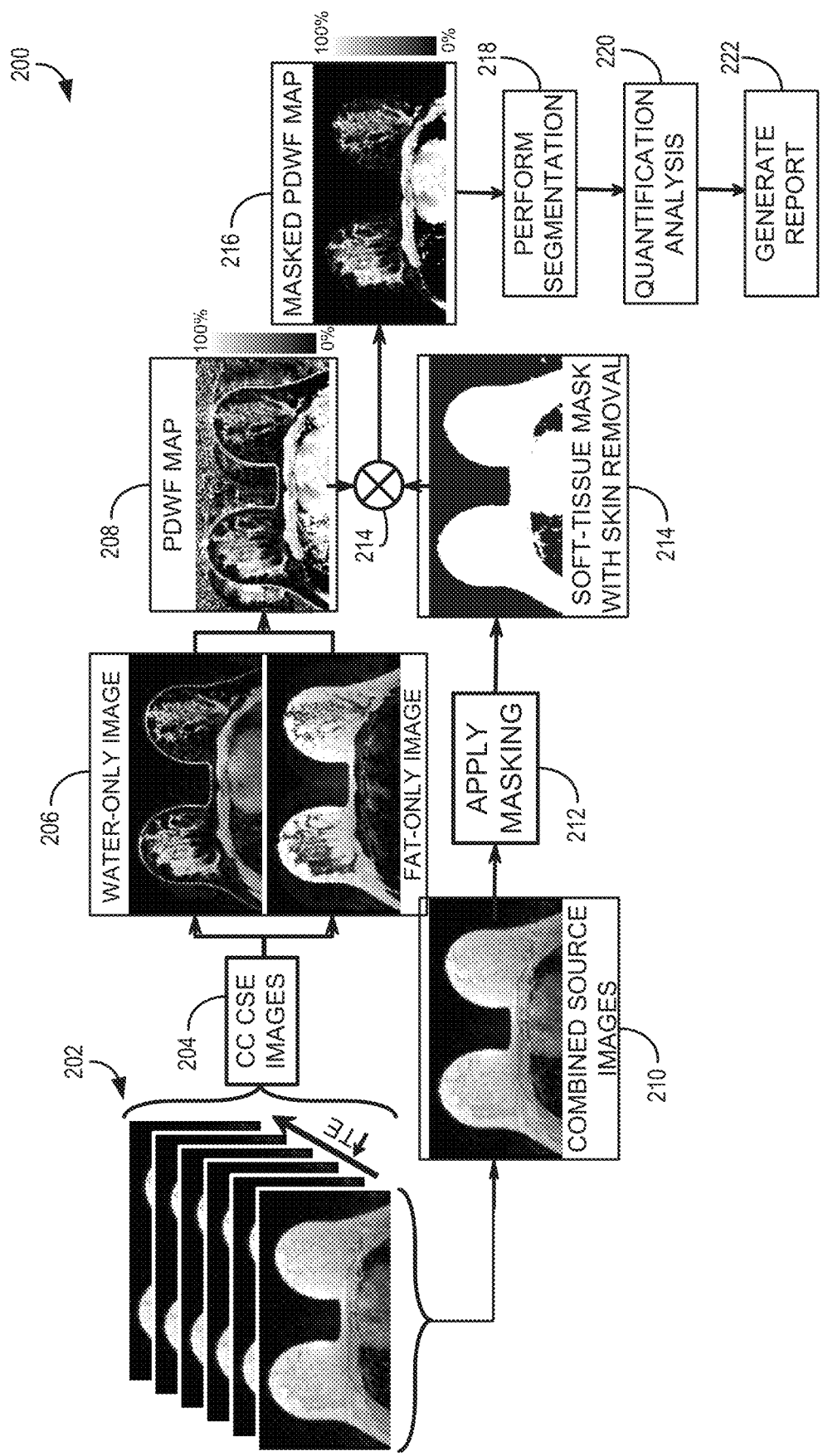
FIG. 2 is a schematic flow chart setting forth steps of a process for assessing tissue in accordance with the present disclosure.

Referring now to FIG. 2, a schematic flow diagram 200 is provided to illustrate non-limiting example steps of a process for creating PDWF maps using confounder-corrected CSE-MRI (CC CSE-MRI). First, data acquisition 202 is performed to acquire MRI data, such as using the MRI system 100 described above with respect to FIG. 1. For example, a multi-echo pulse sequence may be used to acquire multiple complex images at different echo times that are reconstructed at process block 204.

A low flip angle can be used to control or minimize $T_1$ related bias. For example, a low-flip angle acquisition may be performed with a multi-echo CSE-MRI pulse sequence, such as multi-peak Iterative decomposition of water and fat with echo asymmetry and least-squares estimation (IDEAL), for example, available from General Electric MRI systems as "IDEAL IQ." Much larger differences are seen with a $T_1$ weighted acquisition using a 2-point Dixon method, such as "VIBRANT-Flex" available from General Electric MRI systems or other Dixon-based methods available form Siemens (2-point Dixon or Dixon-VIBE), Philips (mDixon or mDixon-quant), and others. One of ordinary skill in the art will recognize that a low flip angle in this context is a function of TR. For example, a flip angle of 35 degrees with a TR of 10 ms is high and will lead to considerable T1 weighting. On the other hand, a flip angle of 35 degrees with a TR of 4,000 ms is quite low. However, such considerations for selecting sizes of flip angles (i.e., "high" or "low") are within the skill of one of ordinary skill in the art. Notably, the use of a low flip angle is but one mechanism that can be used to control T1 weighting. Other examples include adjusting the TR of the acquisition or the use of lookup tables or empirical correction methods to account for T1 weighting.

In the illustrated, non-limiting example, the number of images may be six, but could be any number of two or more echoes. The choice of echo times can be selected to maximize the noise performance of the subsequent water-fat separation.

The CC CSE-MRI images 204 can be subjected to a water-fat separation algorithm at process block 206 that using region growing or other related methods to avoid water-fat swaps and create separated water and fat images, as illustrated. The effects of $T_2^*$ decay can be avoided through simultaneous estimation of water, fat, and $R_2^*$ as previously described by Yu et al. (described in Yu H, McKenzie C A, Shimakawa A, Vu A T, Brau A C, Beatty P J, Pineda A R, Brittain J H, Reeder S B. Multiecho reconstruction for simultaneous water-fat decomposition and T2* estimation. J Magn Reson Imaging 2007; 26(4):1153-61; Yu H, Shimakawa A, McKenzie C A, Brodsky E, Brittain J H, Reeder S B. Multiecho water-fat separation and simultaneous R2* estimation with multifrequency fat spectrum modeling. Magn Reson Med 2008; 60(5):1122-34; and U.S. Pat. Nos. 7,468,605 and 7,924,003, all of which are incorporated herein by reference in its entirety). Accurate separation of water and fat can be achieved by using multi-peak spectral modeling of fat, and the effects of eddy currents should also be addressed, such as described in Hernando D, Hines C D, Yu H, Reeder S B. Addressing phase errors in fat-water imaging using a mixed magnitude/complex fitting method. Magn Reson Med 2012; 67(3):638-44. And Yu H, Shimakawa A, Hines C D, McKenzie C A, Hamilton G, Sirlin C B, Brittain J H, Reeder S B. Combination of complex-based and magnitude-based multiecho water-fat separation for accurate quantification of fat-fraction. Magn Reson Med 2011; 66(1):199-206, and U.S. patent application Ser. No. 13/089,512, filed Apr. 19, 2011, each of which is incorporated herein by reference in its entirety.

At process block 208, the separated water and fat images are then recombined, for example, on a pixel-by-pixel basis into a PDWF map. The effects of noise related bias at low water-fraction can be controlled by using methods such as magnitude discrimination, analogous to what has been used for fat-fraction maps, such as described in Liu C Y, McKenzie C A, Yu H, Brittain J H, Reeder S B. Fat quantification with IDEAL gradient echo imaging: correction of bias from T(1) and noise. Magn Reson Med 2007; 58(2):354-64. And U.S. Pat. No. 8,000,769, which are incorporated herein by reference in its entirety. If the underlying signals are confounder-corrected, the then resulting PDWF map will be a good estimate of the PDWF.

It is desirable that the PDWF values in the background noise regions where there is no tissue be controlled. One approach to achieve such control is to use a mask. For example, at process block 210 an average, maximum intensity projection, or other combination of the magnitude of the source echo image data 202 can be used to combine the source images. From that, at process block 212 a masking algorithm can be applied to mask areas where there the signal is not present, or is below a threshold. For example, the masking algorithm can include k-means algorithm, such as described in Lloyd S. Least squares quantization in PCM, IEEE Trans Info Theory 1982; 28:129-137, which is incorporated herein by reference in its entirety, or other algorithms that can mask areas where there is very low or no signal. Further, at process block 214, it may be desirable to mask the high water signal from skin, which can be removed using region contraction methods at the border of the tissue. Masking of skin may be desirable when attempting to quantify fibroglandular tissue (FGT), for example. As such, this step may be included in the masking algorithm, or as a separate step. Finally, the mask can be applied to the PDWF map from process block 208 to generate a "masked" PDWF map at process block 216, for subsequent analysis.

For example, at process block 218, a segmentation process can be performed to facilitate the generation of a report that may include quantification of, for example, FGT. The segmentation process, as will be described, may take a variety of forms. However, once the images are segmented, quantification analysis can be performed at process block 220 to facilitate the creation of a report at process block 222. For example, the average density of FGT in breast is a single quantity that can be estimated by dividing the effective volume of FGT ($V_{FGT}$) by the total volume of the segmented breast tissue, which is given by:

$$\hat{v} = \frac{\int_{ROI} v(r)dr}{\int_{ROI} dr}; \quad (11)$$

or discretely, $$\hat{v} = \frac{\sum_{ROI} v(r)}{N}; \quad (12)$$

where N is the number of voxels in the region of the segmented breast issue.

These two metrics of PDWF-based breast density provide useful metrics of both the total FGT volume content of the breast as well as the average density (concentration) of FGT in the breast. Other variations, such as regional average concentration of FGT may also be calculated and included in the report at process block 222.

In order to quantify the total water containing tissue in the breast, segmentation of the breast and integration of the PDWF over the entire breast can be performed to yield the total volume of fibroglandular tissue. However, it should be noted the proton density of water in adipose tissue is non-zero, due to the presence of blood vessels and other water-based organelles and water containing tissue, typically on the order of 5-10% water signal. Therefore, correction for the water content of adipose tissue can be performed. This can be achieved in part through thresholding of voxels containing predominantly adipose tissue, excluding those voxels containing little or no FGT.

A thresholding approach does not, however, account for voxels with partial volume mixtures of FGT and adipose tissue and a more general approach is valuable. For a voxel at position r containing a mixture of FGT and adipose tissue, the measured PDWF will be given by:

$$\eta'(r) = \eta_{FGT} v(r) + \eta_A (1-v) \quad (13);$$

where $\eta_{FGT}$ and $\eta_A$ are spatially independent PDWF values of "pure" FGT and adipose tissue, respectively, and v(r) is the fraction of FGT in the voxel in question. Generally, an assignment of $\eta_{FGT}=1.0$ can be made, which assumes that that $\eta_A$ is known. $\eta_A$ can be measured experimentally. Rearranging equation 13, the corrected fraction of FGT in the voxel in question is given by:

$$v(r) = \frac{\eta'(r) - \eta_A}{\eta_{FGT} - \eta_A}. \quad (14)$$

It is noted that $v(r)=\eta'(r)$ in the case where $\eta_A=0$ and $\eta_{AFGT}=1.0$. Using equation 14, the total volume of FGT in the segmented region of interest (ROI) over the breast can be determined by the integral over the ROI, which is given by:

$$V_{FGT} = \int_{ROI} v(r) dr \quad (15);$$

or discretely, $$V_{FGT} = \Delta V \Sigma_{ROI} v(r) \quad (16);$$

where $\Delta V$ is the voxel volume, providing an estimate of the total effective volume of FGT in the breast. This metric represents a quantitative biomarker of the effective volume of water-based tissue within the breast, which is predominantly FGT. Of course, other metrics can be readily derived from and used with or instead of total effective volume of FGT in the breast. For example, average concentration of FGT and other metrics may also be suitable biomarkers. Also, any metric can be provided for individual breasts, or can be assessed across the collective breast tissue of both breasts.

The above-described process is one example in accordance with the present disclosure. For example, as described above, PDFF or PDWF can be estimated from separated water and fat images. However, it is also possible to estimate the PDFF or PDWF directly from the source echo images, rather than requiring that separated water and fat images are estimated first. In this case, the signal model is typically written such that they signal at an echo time $TE_n$ (n=1 . . . N) is:

$$s(TE_n) = (W + Fc^n)^{(i2\pi\psi TE_n)(-TE_n/T2^*)}; \quad (17)$$

where cn is the sum of weighted exponentials at time $TE_n$ based on multi-peak modeling and $\psi$ is a field map in Hz. Thus, $s(TE_n)$ is measured and, knowing $TE_n$ and $c^n$, separated water images (W) and fat images (F) can be estimated, as well as a field map image ($\psi$) and a T2* image.

Thus, equation 17 can be rewritten as:

$$s(TE_n) = A(PDWF + (1 - PDWF) * cn)^{(i2\pi\psi TE_n)(-TE_n/T2)}; \quad (18)$$

Where W=A(PDWF) and F=A(1−PDWF). In this way, A and PDWF can be estimated directly from the source echo images 204, rather than needing to first create separate water-only and fat-only images 206.

Figure 3:
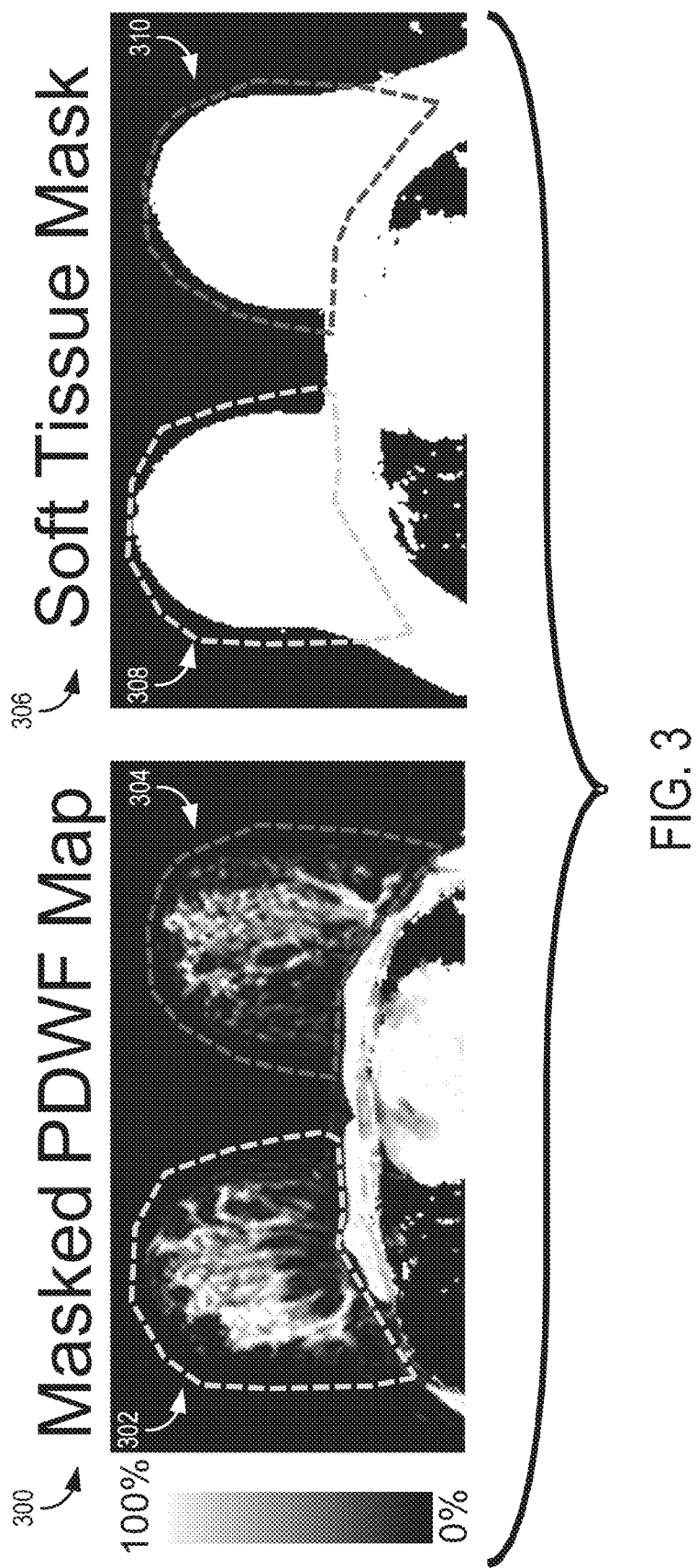
FIG. 3 is a set of images illustrating a segmentation process in accordance with the present disclosure.

Turning to FIG. 3, an example of a segmentation of a single-slice (from a 3D volume of many slices covering both breasts) masked PDWF map is illustrated, which is segmented to calculate the total volume of FGT in that slice, according to equation 15. In particular, regions of the masked PDWF map 300 are segmented to create a PDWF map right breast segment 302 and a PDWF map left breast segment 304 over all slices to estimate volume of fibroglandular tissue (VFG). Also, regions of the soft-tissue mask 306 are segmented to create a soft-tissue mask right breast segment 308 and a soft-tissue mask left breast segment 310 over all slices to estimate volume (VB). With general segmentation such as this, over the entire breast, the total volume of FGT of each breast can be estimated. Further, using identical regions of interest (ROI) on the tissue mask, the total volume of each breast can also be estimated.

Figure 4:
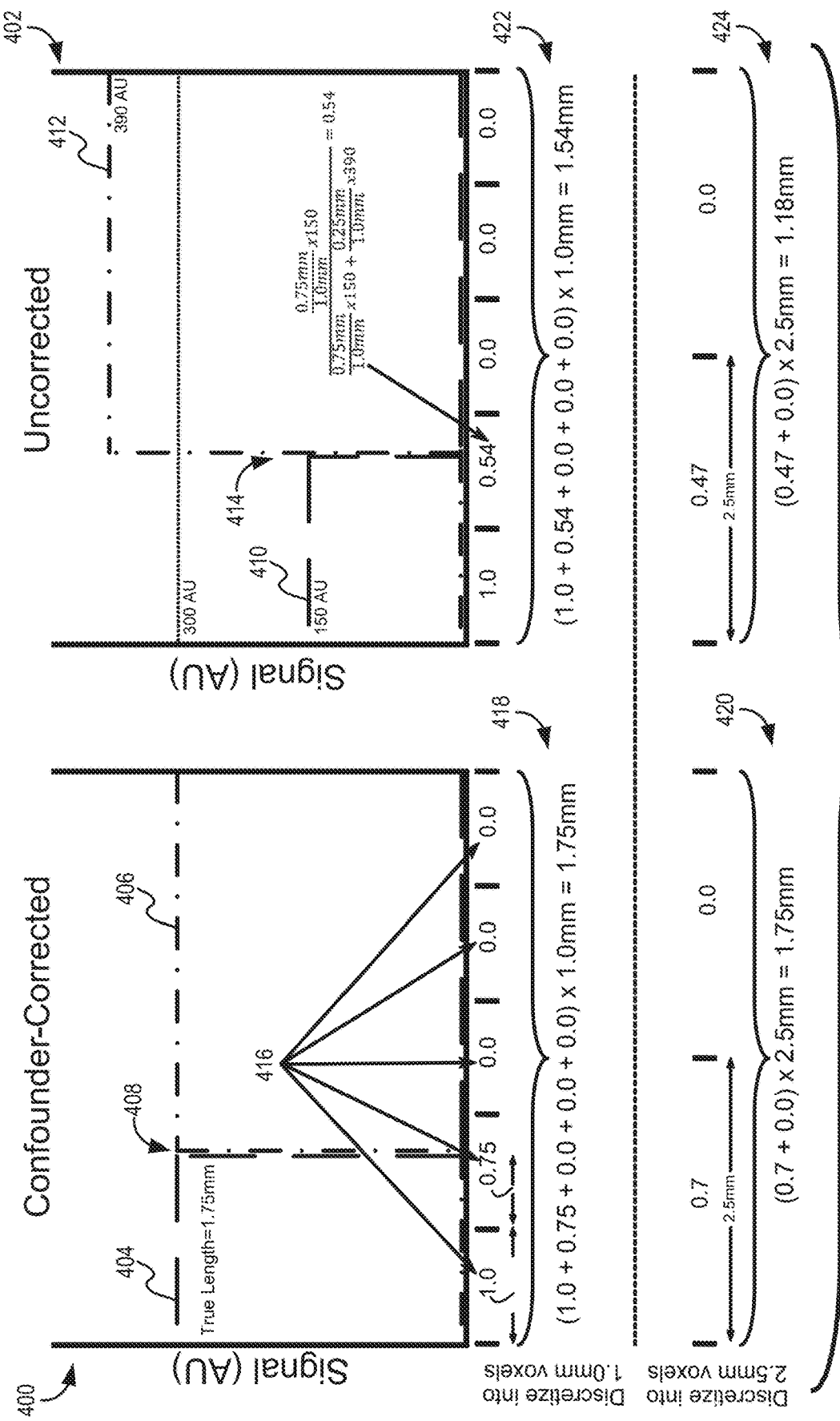
FIG. 4 is a set of correlated graphs providing a one-dimensional schematic that explains how to use confounder-corrected data to discern tissue properties with greater accuracy and consistency than with traditional data, in accordance with the present disclosure.

Referring to FIG. 4, a pair of graphs are provided that illustrate in great detail how accurate estimates of FGT can be obtained, accounting for the effects of partial volume effects, using a non-limiting one-dimensional example. In this example, a sharp junction is used between FTG, with $\eta_{FGT}=1.0$ and adipose tissue (with $\eta_A=0$, for simplicity). In particular, a first graph 400 is provided that illustrates an estimation of water volume using confounder-corrected PDWF and shows that it is robust to changes in spatial resolution. A second graph 402 is provided that is correlated with the first graph 400, but uses an uncorrected PDWF, and illustrates that estimations based thereon are prone to error and that the error can be exacerbated by resolution.

Specifically, the graph of confounder-corrected data 400 shows a water signal 404 and a fat signal 406 and illustrates a water-fat interface 408. As can be seen, the water signal 404 and fat signal 406 are similar, such as would occur with confounder-corrected water-fat separation. This stands in contrast to the graph of uncorrected data 402, where the water signal 410 and fat signal 412 share the same water-fat interface 414, but the signals 410, 412 are quite distinct, for example, due to $T_1$ bias. In the confounder-corrected data 400, when the signal is discretized and the PDWF is calculated for each voxel, partial volume effects are automatically accounted for, as illustrated by the calculations 416. This leads to robust estimates of PDWF, independent of the spatial resolution. In particular, as illustrated, the confounder-corrected data 400 provides the correct estimate of length of water containing voxel for both 1.0 mm voxels 418 and 2.5 mm voxels 420. Thus, the estimates of FGT are robust to partial volume effects and voxel size. However, when the water and fat signals are different, such as due to confounding factors illustrated in the uncorrected data 402, the resulting PDWF estimates 422 can be erroneous and depend strongly on the size of the voxel in areas of partial volume effects 424. That is, with the uncorrected data 402, total estimated amount of FGT will depend on the spatial resolution, as well as the effects of acquisition protocol and reconstruction algorithm.

EXAMPLE

In one, non-limiting example, the above-described systems and methods were performed and studied. In this non-limiting example, after obtaining IRB approval for this HIPAA compliant study, six volunteers were consented to undergo confounder-corrected CSE-MRI with a 3T MRI acquisition.

Magnetic Resonance Imaging Protocol.

Quantitative confounder-corrected CSE-MRI acquisition was performed using a 3T clinical MRI system using an 8 channel dedicated breast coil. Patients were imaged in a standard prone position, with the following acquisition parameters: Images were obtained with a confounder-corrected CSE-MRI sequence with a 32 cm axial field-of-view, bandwidth of ±90.91, TR=8.8 ms, and six echoes (TEs=1.0, 2.0, 3.1, 4.1, 5.2, and 6.2 ms). A low flip angle of 1° was used to minimize T1 related bias. Further, images were obtained with two protocols, each with different spatial resolution. Protocol 1: voxel 1.4×2.0×3.0 mm$^3$ and Protocol 2: voxel 2.0×2.2×50 mm$^3$. Scan time for Protocols 1 and 2 was 105 s and 60 s, respectively. Complex combined real and imaginary images were saved offline for reconstruction of PDWF maps.

Raw complex images were used by an offline reconstruction algorithm that used a non-linear least-squares fit to provide simultaneous estimation of water and fat images as well as an R2* map and B$_0$ magnetic field inhomogeneity maps. This algorithm also used spectral modeling of fat for accurate water-fat signal separation, and a mixed fitting strategy to avoid the effects of eddy current. Water-fat "swaps" were avoided by using an advanced region growing algorithm based on smoothness assumptions of the B$_0$ field inhomogeneity map, as describe in Hernando D, Kellman P, Haldar J P, Liang Z P. Robust water/fat separation in the presence of large field inhomogeneities using a graph cut algorithm. Magn Reson Med 2010; 63(1):79-90, which is incorporated herein by reference in its entirety. In this way, the separated water and fat images are corrected for R2* decay and magnetic field inhomogenities. Water and fat images were combined into a PDWF map based on the magnitude discrimination technique, in order to avoid noise related bias.

Data Analysis.

PDWF maps were calculated as described above and were provided for each patient, providing full coverage of both breasts. Segmentation of each breast was performed as described above in order to calculate the average PDWF over the entire breast, as well as the total volume of each breast and skin removal was accomplished using an erosion operation in Matlab (MathWorks, Natick, Mass.). Segmentation was performed over a 6 cm axial slab covering the central portion of the bilateral breasts for both protocols, producing the ROIs used in this analysis. The total volume of both breasts ($V_B$) was calculated using the ROI. The volume of FGT ($V_{FGT}$) was calculated by integration of the PDWF maps over the ROI. Concentration of FGT is defined at $V_{FGT}/V_B \times 100$. Bland-Altman analysis was performed to compare VFGT between protocols.

Table 1 lists the $V_{FGT}$ and FGT concentrations for the six volunteers by protocol.

TABLE 1

| Volunteer | Concentration FGT (%) | | Volume FGT (cm$^3$) | |
|---|---|---|---|---|
| | Protocol 1 | Protocol 2 | Protocol 1 | Protocol 2 |
| 1 | 36.6 | 37.1 | 132 | 135 |
| 2 | 8.3 | 9.5 | 97 | 110 |
| 3 | 34.1 | 34.9 | 97 | 98 |
| 4 | 81.2 | 82 | 225 | 233 |
| 5 | 32.8 | 33 | 276 | 277 |
| 6 | 72.5 | 73.7 | 388 | 399 |

Both volume and concentration of FGT correspond with expected results given the visual appearance of the FGT. Bland-Altman plots of the $V_{FGT}$ demonstrated excellent agreement between methods.

The measured volume and concentration of FGT demonstrated excellent agreement between the two CSE-MRI protocols. Thus, the present disclosure using CSE-MRI methods to quantify the volume and concentration of FGT is based on a fundamental property of tissue, i.e.: PDWF. This approach differs from the subjective evaluation of breast density in routine clinical practice, i.e.: the mammographic appearance of radiodense FGT relative to radiolucent fat, which is limited due to intra- and inter-reader variability and lack of quantitation. The PDWF reflects a quantitative measurement of FGT corrected for relevant confounding factors over a wide range of acquisition protocols. This technique eliminates the dependence on voxel size avoiding measurement error caused by partial volume average in of fat and FGT (unavoidable in the breast, where fat and FGT are intermingled), and is thus robust to change in spatial resolution, as demonstrates. The method provides systems and methods to analyze breast density without the use of ionizing radiation and, furthermore, provides more precise, reproducible, and accurate quantification metrics of FGT, independent of the spatial resolution used for imaging, and multiple other confounders, which is a more objective analysis than the traditional qualitative determination of mammographic breast density.

Thus, the present disclosure provides a system for acquiring MR data and processing such data to yield a metric for quantifying the amount and concentration of breast fibroglandular tissue as a precise, accurate, and reproducible biomarker of breast density. The systems and methods do not use ionizing radiation, but are based on confounder corrected CSE-MRI derived proton density water fraction in the breast. Unlike mammography, PDWF maps over the entire breast and provide a means to estimate the total volume of FGT and also the average concentration of FGT over the entire breast. Thus, objective, repeatable, quantified metrics are provided that, as demonstrated above, demonstrate the feasibility of these MR-based biomarkers for quantifying breast density.

Notably, PDWF, unlike other efforts to perform MR-based breast density measurements, provides a metric that is corrected for all known confounders of the MR signal. As such, changes in acquisition parameters such as flip angle, TR, TE, spatial resolution have minimal impact on final estimates of MR-based breast density. Further, quantitative CSE-MRI methods for quantifying PDFF are now commercially available on all major MRI vendors. These methods have been shown to be highly reproducible across vendors and field strength, providing a valid, reliable and standardized biomarker, PDFF, for quantifying tissue fat content.

These metrics correlated with the cross-sectional, 3D image data provided by MRI, offer a new and rapid means for providing accurate, precise, robust and reproducible measure of breast density without the need for ionizing radiation or substantial additions in scan time or the use of contrast. The addition of this rapid scan to standard breast MRI, which is increasingly recommended for high risk patients with certain risk factors for the future development of breast cancer, can provide a standardized MRI-based metric of breast density. Therefore, PDWF in the breast presents a viable MR-based metric of fibroglandular tissue density.

In summary, we have introduced, developed and demonstrated the feasibility a new MR-based metric for breast density, the proton density water fraction (PDWF) as a feasible metric to quantify the total volume and average concentration of FGT in the breast.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for assessing tissue properties of a subject within a region of interest (ROI) using a magnetic resonance imaging (MRI) system, the method including steps comprising:
   (i) acquiring chemical-shift-encoded imaging data of the ROI, wherein the ROI includes a breast of the subject;
   (ii) from the imaging data, determining a proton density water fraction (PDWF) map;
   (iii) using the PDWF map, quantifying a property of tissue within the ROI;
   (iv) determining a volume of the breast and a volume of fibroglandular tissue (FGT) in the breast; and
   (v) using the PDWF map and one of the volume of the breast or the volume of the FGT, generating a report indicating the quantified property of the tissue.

2. The method of claim 1 wherein step (i) includes performing a pulse sequence using the MRI system to chemical-shift-encoded imaging data.

3. The method of claim 2 wherein pulse sequence includes a flip angle selected to control $T_1$ related bias.

4. The method of claim 3 wherein the flip angle is low, relative to the TR, to control T1 weighting.

5. The method of claim 1 wherein the PDWF is free errors cause by partial volume effects.

6. The method of claim 1 wherein step (ii) includes determining a proton density fat fraction (PDFF) and calculating PDWF as 1 minus PDFF.

7. A method for assessing tissue properties of a subject within a region of interest (ROI) using a magnetic resonance imaging (MRI) system, the method including steps comprising:
   (i) acquiring chemical-shift-encoded imaging data of the ROI;
   (ii) from the imaging data, determining a proton density water fraction (PDWF) map;
   (iii) using the PDWF map, quantifying a property of tissue within the ROI;
   (iv) using the PDWF map, generating a report indicating the quantified property of the tissue; and
   wherein step (i) includes processing the chemical-shift-encoded imaging data using a region growing method to control water-fat swaps and create chemical-shift-encoded, water-fat separated data from the ROI.

8. The method of claim 7 wherein the ROI includes a breast and wherein quantified property of the tissue includes a quantified concentration of fibroglandular tissue in the breast.

9. The method of claim 8 wherein step (iv) further includes a step of determining a volume of the breast and a volume of fibroglandular tissue (FGT) in the breast.

10. The method of claim 9 wherein the property of the tissue is a concentration of FGT in the breast.

11. The method of claim 10 wherein the average concentration of FGT in the breast is calculated as a ratio of volume of FGT in the breast to volume of the breast.

12. The method of claim 7 wherein step (ii) includes combining the chemical-shift-encoded, water-fat separated data to create the PDWF map.

13. The method of claim 12 further comprising combining the chemical-shift-encoded, water-fat separated data on a pixel-by-pixel basis to create the PDWF map.

14. The method of claim 7 further comprising using a mask to control influence of values in the PDWF map that include background noise.

15. The method of claim 7 further comprising performing a segmenting process to remove portions of the ROI that do not include the tissue.

16. A method for assessing tissue properties of a subject within a region of interest (ROI) using a magnetic resonance imaging (MRI) system, the method including steps comprising:
   (i) acquiring chemical-shift-encoded imaging data of the ROI;
   (ii) from the imaging data, determining a proton density water fraction (PDWF) map;
   (iii) using the PDWF map, quantifying a property of tissue within the ROI;
   (iv) using the PDWF map, generating a report indicating the quantified property of the tissue; and
   further comprising performing a thresholding of voxels containing predominantly adipose tissue to control for water content of adipose tissue in the ROI.

17. A magnetic resonance imaging (MRI) system comprising:
   a magnet system configured to generate a polarizing magnetic field about at least a portion of a subject arranged in the MRI system;
   a plurality of gradient coils configured to apply a gradient field to the polarizing magnetic field;
   a radio frequency (RF) system configured to apply an excitation field to the subject and acquire MR image data from a ROI;
   a computer system programmed to:
     receive chemical-shift-encoded data of the ROI acquired using the RF system and gradient coils;
     analyze the chemical-shift-encoded data, to determine a water component and fat component;
     using the chemical-shift-encoded data, the water component, and the fat component, determine a proton density water fraction (PDWF) map;
     using the PDWF map, quantify a property of tissue within the ROI;
     using the PDWF map, generate a report indicating the quantified property of the tissue;
   wherein the ROI includes a breast and wherein quantified property of the tissue includes a quantification of at least one of concentration or volume of fibroglandular tissue in the breast; and
   wherein the computer system is further programmed to determine a volume of the breast and a volume of fibroglandular tissue (FGT) in the breast.

18. The system of claim 17 wherein the property of the tissue includes at least one of a concentration or a volume of FGT in the breast.

19. The system of claim 18 wherein the computer system is further programmed to calculate the concentration of FGT in the breast as a ratio of volume of FGT in the breast to volume of the breast.

20. The system of claim 17 wherein the computer system is further programmed to estimate one of PDFF or PDWF directly from chemical-shift-encoded data.

21. A magnetic resonance imaging (MRI) system comprising:
a magnet system configured to generate a polarizing magnetic field about at least a portion of a subject arranged in the MRI system;
a plurality of gradient coils configured to apply a gradient field to the polarizing magnetic field;
a radio frequency (RF) system configured to apply an excitation field to the subject and acquire MR image data from a ROI;
a computer system programmed to:
receive chemical-shift-encoded data of the ROI acquired using the RF system and gradient coils;
analyze the chemical-shift-encoded data, to determine a water component and fat component;
using the chemical-shift-encoded data, the water component, and the fat component, determine a proton density water fraction (PDWF) map;
using the PDWF map, quantify a property of tissue within the ROI;
using the PDWF map, generate a report indicating the quantified property of the tissue; and
wherein the PDWF is free of errors cause by partial volume effects.

22. A magnetic resonance imaging (MRI) system comprising:
a magnet system configured to generate a polarizing magnetic field about at least a portion of a subject arranged in the MRI system;
a plurality of gradient coils configured to apply a gradient field to the polarizing magnetic field;
a radio frequency (RF) system configured to apply an excitation field to the subject and acquire MR image data from a ROI;
a computer system programmed to:
receive chemical-shift-encoded data of the ROI acquired using the RF system and gradient coils;
analyze the chemical-shift-encoded data, to determine a water component and fat component;
using the chemical-shift-encoded data, the water component, and the fat component, determine a proton density water fraction (PDWF) map;
using the PDWF map, quantify a property of tissue within the ROI;
using the PDWF map, generate a report indicating the quantified property of the tissue; and
wherein, to determine the PDWF, the computer system is further programmed to determine a proton density fat fraction (PDFF) and calculating PDWF as 1 minus PDFF.

23. A magnetic resonance imaging (MRI) system comprising:
a magnet system configured to generate a polarizing magnetic field about at least a portion of a subject arranged in the MRI system;
a plurality of gradient coils configured to apply a gradient field to the polarizing magnetic field;
a radio frequency (RF) system configured to apply an excitation field to the subject and acquire MR image data from a ROI;
a computer system programmed to:
receive chemical-shift-encoded data of the ROI acquired using the RF system and gradient coils;
analyze the chemical-shift-encoded data, to determine a water component and fat component;
using the chemical-shift-encoded data, the water component, and the fat component, determine a proton density water fraction (PDWF) map;
using the PDWF map, quantify a property of tissue within the ROI;
using the PDWF map, generate a report indicating the quantified property of the tissue; and
wherein the computer system is further programmed to process the chemical-shift-encoded data using a region growing method to control water-fat swaps and create at least one water-only image and at least one fat-only image.

24. The system of claim 23 wherein the computer system is further programmed to combine the at least one water-only image and at least one fat-only image to create the PDWF map.

25. The system of claim 24 wherein the computer system is further programmed to combine the at least one water-only image and at least one fat-only image on a pixel-by-pixel basis to create the PDWF map.

26. A magnetic resonance imaging (MRI) system comprising:
a magnet system configured to generate a polarizing magnetic field about at least a portion of a subject arranged in the MRI system;
a plurality of gradient coils configured to apply a gradient field to the polarizing magnetic field;
a radio frequency (RF) system configured to apply an excitation field to the subject and acquire MR image data from a ROI;
a computer system programmed to:
receive chemical-shift-encoded data of the ROI acquired using the RF system and gradient coils;
analyze the chemical-shift-encoded data, to determine a water component and fat component;
using the chemical-shift-encoded data, the water component, and the fat component, determine a proton density water fraction (PDWF) map;
using the PDWF map, quantify a property of tissue within the ROI;
using the PDWF map, generate a report indicating the quantified property of the tissue; and
wherein the computer system is further programmed to use a mask to control influence of values in the PDWF map that include background noise.

27. A magnetic resonance imaging (MRI) system comprising:
a magnet system configured to generate a polarizing magnetic field about at least a portion of a subject arranged in the MRI system;
a plurality of gradient coils configured to apply a gradient field to the polarizing magnetic field;
a radio frequency (RF) system configured to apply an excitation field to the subject and acquire MR image data from a ROI;
a computer system programmed to:
receive chemical-shift-encoded data of the ROI acquired using the RF system and gradient coils;
analyze the chemical-shift-encoded data, to determine a water component and fat component;

using the chemical-shift-encoded data, the water component, and the fat component, determine a proton density water fraction (PDWF) map;

using the PDWF map, quantify a property of tissue within the ROI;

using the PDWF map, generate a report indicating the quantified property of the tissue; and wherein the computer system is further programmed to perform a segmenting process to remove portions of the ROI that do not include the tissue.

28. A magnetic resonance imaging (MRI) system comprising:

a magnet system configured to generate a polarizing magnetic field about at least a portion of a subject arranged in the MRI system;

a plurality of gradient coils configured to apply a gradient field to the polarizing magnetic field;

a radio frequency (RF) system configured to apply an excitation field to the subject and acquire MR image data from a ROI;

a computer system programmed to:

receive chemical-shift-encoded data of the ROI acquired using the RF system and gradient coils;

analyze the chemical-shift-encoded data, to determine a water component and fat component;

using the chemical-shift-encoded data, the water component, and the fat component, determine a proton density water fraction (PDWF) map;

using the PDWF map, quantify a property of tissue within the ROI;

using the PDWF map, generate a report indicating the quantified property of the tissue; and wherein the computer system is further programmed to perform a thresholding of voxels containing predominantly adipose tissue to control for water content of adipose tissue in the ROI.

* * * * *